US010952717B2

(12) United States Patent
Rodriguez Salazar et al.

(10) Patent No.: US 10,952,717 B2
(45) Date of Patent: Mar. 23, 2021

(54) TISSUE RETRACTION BANDS AND METHODS OF USE THEREOF

(71) Applicant: Boston Scientific Scimed, Inc., Maple Grove, MN (US)

(72) Inventors: Juan C. Rodriguez Salazar, Watertown, MA (US); Jose Garcia-Cordero, Ocala, FL (US); Anne Sluti, Watertown, MA (US); Caroline Riedel, Westford, MA (US); Talha Riaz, Framingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/930,613

(22) Filed: May 13, 2020

(65) Prior Publication Data

US 2020/0360005 A1    Nov. 19, 2020

Related U.S. Application Data

(60) Provisional application No. 62/908,972, filed on Oct. 1, 2019, provisional application No. 62/848,815, filed on May 16, 2019.

(51) Int. Cl.
*A61B 17/02* (2006.01)
*A61B 1/00* (2006.01)
(Continued)

(52) U.S. Cl.
CPC ........ *A61B 17/0293* (2013.01); *A61B 1/0014* (2013.01); *A61B 1/00135* (2013.01);
(Continued)

(58) Field of Classification Search
CPC ...... A61B 2017/00818; A61B 17/0218; A61B 1/00135; A61B 1/0014
See application file for complete search history.

(56) References Cited

U.S. PATENT DOCUMENTS 8,403,837 B2 *   3/2013   Okoniewski ....... A61B 17/0218
                                                    600/201
10,143,459 B2    12/2018   Heftman
(Continued)

FOREIGN PATENT DOCUMENTS

CN    209611212 U    11/2019
CN    110731802 A     1/2020
(Continued)

OTHER PUBLICATIONS

International Search Report and Written Opinion for the International Patent Application No. PCT/US2020/032581, dated Aug. 24, 2020, 14 pages.
(Continued)

*Primary Examiner* — Christian A Sevilla
(74) *Attorney, Agent, or Firm* — Kacvinsky Daisak Bluni PLLC

(57) ABSTRACT

The present disclosure relates generally to the field of medical devices. In particular, the present disclosure relates to a tissue traction device for endoscopic procedures such as tissue dissection. For example, a tissue traction device may include first and second attachment members pivotably attached by first and second swivels to opposite ends of a stretchable traction band comprising a compliant or semi-compliant material.

20 Claims, 4 Drawing Sheets

(51) Int. Cl.
*A61B 90/00* (2016.01)
*A61B 17/00* (2006.01)

(52) U.S. Cl.
CPC .............. *A61B 17/0218* (2013.01); *A61B 2017/00292* (2013.01); *A61B 2017/00818* (2013.01); *A61B 2090/0807* (2016.02)

(56) References Cited

U.S. PATENT DOCUMENTS

| | | | |
|---|---|---|---|
| 2005/0250988 A1* | 11/2005 | Ewers | A61B 1/0014 600/102 |
| 2007/0250116 A1 | 10/2007 | Raju | |
| 2011/0137129 A1* | 6/2011 | Heinrich | A61B 17/00234 600/206 |
| 2012/0078057 A1* | 3/2012 | Scott | A61B 17/06109 600/201 |
| 2018/0035997 A1 | 2/2018 | Smith et al. | |
| 2018/0092523 A1* | 4/2018 | Smith | A61B 1/32 |
| 2018/0263614 A1* | 9/2018 | Lee | A61B 17/0218 |
| 2020/0129181 A1 | 4/2020 | Carrillo, Jr. et al. | |

FOREIGN PATENT DOCUMENTS

| | | |
|---|---|---|
| JP | 2008062004 A | 3/2008 |
| WO | 2020015692 A1 | 1/2020 |

OTHER PUBLICATIONS

Ge et la., "A novel clip-band traction device to facilitate colorectal endoscopic submucosal dissection and defect closure", Tools and Techniques, VideoGie 2020, vol. 5, No. 5.
Imaeda, H. et al., "Advanced Endoscopic Submucosal Dissection with Traction", World Journal of Gastrointestinal Endoscopy 6(7):286-295 (2014).
Ritsuno, H., et al., "Prospective Clinical Trial of Traction Device-Assisted Endoscopic Submucosal Dissection of Large Superficial Colorectal Tumors Using the S-O Clip", Surg. Endosc. (2014) 28:3143-3149.
Sakamoto N. et al., "The Facilitation of a New Traction Device (S-O Clip) Assisting Endoscopic Submucosal Dissection for Superficial Colorectal Neoplasms", Endoscopy 2008; 40:E94-95.
Sakamoto N. et al., "Endoscopic Submucosal Dissection of Large Colorectal Tumors by Using a Novel Spring-Action S-O Clip for Traction" (with video), Gastrointestinal Endoscopy 69(7):1370-74 (2009).
Takeda T et al., "Traction Device to Remove an Adenoma in the Appendiceal Orifice by Endoscopic Submucosal Dissection", Endoscopy 2013; 45:E239-E240.
Chen et al., "A Clinical Comparative Study of Rubber Ring Versus Dental Floss Combined with Hemoclipping Assisted Endoscopic Submucosal Dissection on Gastrointestinal Tumor" Journal of Shanghai Jiao Tong University (Medical Science) vol. 37 No. 7 Jul. 2017.
Sato-Uemura et al., "Endolifter, a new tool for safe and rapid submucosal endoscopic dissection" Gastroenterology Magazine of Mexico, 2014;79(3):161-165.

* cited by examiner

TISSUE RETRACTION BANDS AND METHODS OF USE THEREOF

CROSS-REFERENCE TO RELATED APPLICATION

The present application claims the benefit of priority under 35 U.S.C. § 119 to U.S. Provisional Patent Application 62/848,815, filed May 16, 2019; and U.S. Provisional Patent Application 62/908,972, filed Oct. 1, 2019, both of which applications are incorporated herein by reference in their entireties for all purposes.

FIELD

The present disclosure relates generally to the field of medical devices. In particular, the present disclosure relates to tissue traction devices for endoscopic procedures such as tissue dissection, and related methods of use thereof.

BACKGROUND

A component of accurately and efficiently performing an endoscopic tissue resection/dissection procedure is the ability to maintain traction as the boundaries of the target tissue are dissected. Traction systems that are associated with and/or provided by an endoscopic cap tend to obstruct a physician's view of the target tissue and/or interfere with accessory tools extending alongside or through the endoscope. These complications may directly contribute to increased procedure time, complexity and risk of perforation or bleeding.

A variety of advantageous medical outcomes may therefore be realized by the tissue retraction devices and related methods of use of the present disclosure.

SUMMARY

In one aspect, the present disclosure relates to a tissue retraction/traction device comprising a traction band comprising a compliant or semi-compliant material. A first attachment member may be pivotably attached to a first end of the traction band by a first swivel. A second attachment member may be pivotably attached to a second end of the traction band by a second swivel.

In the described and other embodiments, the compliant or semi-compliant material include rubbers, latex, elastics, thermoplastic elastomer (TPE), or combinations thereof. The first and second attachment members may include a compressible material such as polymers, plastics, shape memory metals, shape memory alloys, or combinations thereof. The first and second swivels may pivot around a longitudinal axis of the traction band. The traction band may be configured to move between a first configuration having a length of approximately 2.5 to 4.5 cm and a second configuration having a maximum length of approximately 15.00 cm. A filament may be disposed along a length of the traction band. The filament may include a substantially non-compliant material configured to limit a maximum extended length of the traction band. The filament may include a substantially compliant or semi-compliant material configured to increase a retraction force of the traction band.

In another aspect, the present disclosure relates to a tissue retraction system comprising a flexible elongate tubular member defining a working channel therethrough. A first endoscopic instrument may be disposed within the working channel. The first endoscopic instrument may include a first tissue clip attached to a distal end of the instrument. A tissue retraction device may be disposed within the working channel. A first attachment member of the tissue retraction device may be engaged with the first tissue clip.

In the described and other embodiments, the first tissue clip may be releasably attachable to the first attachment member of the tissue retraction device. The first tissue clip at a first end of the tissue retraction/traction device may be positionable in a body lumen. A second tissue clip may be positionable in the body lumen and attachable to a second end of the tissue retraction/traction device opposite the first end of the tissue retraction/traction device. A third tissue clip may be positionable in the body lumen and attachable to a portion of the tissue retraction/traction device. The tissue retraction/traction device may include a traction band comprising a compliant or semi-compliant material. A first attachment member may be pivotably attached to a first end of the traction band via a first swivel. A second attachment member may be pivotably attached to a second end of the traction band via a second swivel. The first and second swivels may allow the respective first and second attachment members to pivot around a longitudinal axis of, or otherwise move with respect to, the traction band.

In various embodiments, more than one attachment member may be provided on the second end of the tissue retraction/traction device. A first tissue clip may be releasably attachable to a first attachment member provided on the first end of the tissue retraction/traction device. The first tissue clip and the first attachment member may be engaged with a target tissue in a body lumen. A second tissue clip may be positionable in the body lumen and attachable to an attachment member provided on the second end of the tissue retraction/traction device. The second tissue clip and accompanying attachment member may be engaged with a first portion of anchoring tissue opposite the target tissue. If it is desired to adjust traction on the tissue retraction/traction device, a third tissue clip may be positionable in the body lumen and attachable to a different attachment member provided on the second end of the tissue retraction/traction device. The third tissue clip and accompanying attachment member may be engaged with a second portion of anchoring tissue opposite the target tissue and spaced apart from the first portion of anchoring tissue. If desired, any attachment member at the second end of the tissue retraction/traction device may be cut to release the clips associated therewith.

In yet another aspect, the present disclosure relates to a method comprising inserting in a body lumen a tissue retraction/traction device loaded onto a first tissue clip of a first endoscopic instrument, advancing the first endoscopic instrument through a working channel of an elongate tubular member and beyond a distal end of the elongate tubular member, and engaging a target tissue of the body lumen with the first tissue clip to secure a first end of the tissue retraction/traction device to a wall of the body lumen.

In the described and other embodiments, the method may further include releasing the first tissue clip from the first endoscopic instrument. The method may further include withdrawing the first endoscopic instrument from within the working channel of the elongate tubular member and attaching a second tissue clip to the distal end of the first endoscopic instrument. The method may further include advancing the first endoscopic instrument through the working channel of the elongate tubular member and beyond a distal end of the elongate tubular member and engaging the wall of the body lumen with the second tissue clip to secure a second end of the tissue retraction/traction device to the wall of the body lumen. The first and second tissue clips may be engaged with opposite sides of the body lumen. The method may further include releasing the second tissue clip from the first endoscopic instrument. The method may further include manipulating the target tissue with a medical device attached to a distal end of a second endoscopic instrument.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to tissue retraction/traction devices, systems and methods designed to provide traction within the gastrointestinal tract during a tissue dissection/resection procedure, it should be appreciated that such systems and methods may be used to manipulate a variety of tissues within a variety of different body lumens and/or body passages.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

In various embodiments, the present disclosure relates generally to devices and systems configured to provide tissue retraction and cutting plane visualization independent of an endoscope during an endoscopic submucosal dissection (ESD) procedure.

Figure 1:
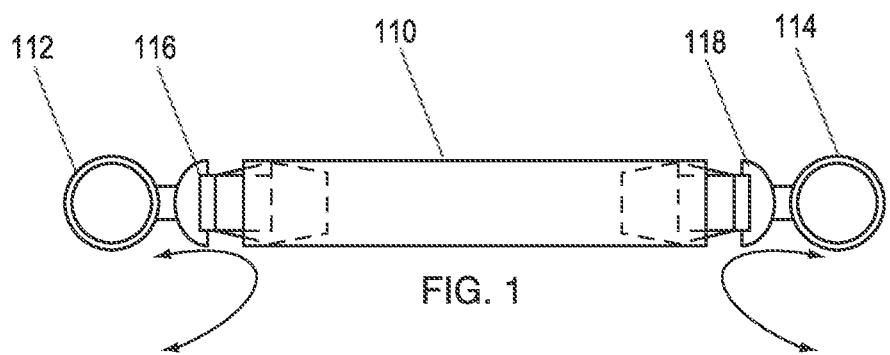
FIG. 1 provides a perspective view of a tissue traction device, according to one embodiment of the present disclosure.

Referring to FIG. 1, in one embodiment, a tissue retraction/traction (such terms being used in the alternative, or simply referenced as "traction" for the sake of simplicity and without intent to limit) device 100 of the present disclosure may include a traction band 110 (e.g., elastic band, tether, stretchable elongate member, etc.) formed from or otherwise comprising a variety of compliant or semi-compliant materials. The traction band 110 may be an elongate cylindrical tube and may be formed hollow or solid. By way of non-limiting example, such materials may include flexible/stretchable rubbers, thermoplastic elastomer (TPE), plastics, polyethylene terephthalate (PET), and the like. A first attachment member 112 (e.g., loop, hook, ring, mini-snare, etc.) may be pivotably attached to a first end of the traction band 110 and a second attachment member 114 (e.g., loop, hook, ring, mini-snare, etc.) may be pivotably attached to a second end of the traction band 110. In various embodiments, the first and second attachment members 112, 114 may comprise a variety of flexible and/or compressible materials configured to compress or fold when disposed, e.g., within the working channel of an endoscopic instrument. Non-limiting examples of such flexible/compressible materials may include flexible plastics, hard rubbers, shape memory metals and/or alloys, and the like. In one embodiment, the first attachment member 112 may be pivotably attached to the first end of the traction band 110 by a first swivel 116 and the second attachment member 114 may be pivotably attached to the second end of the traction band 110 by a second swivel 118. In various embodiments, the first and second attachment members 112, 114 may swivel or pivot or rotate about or otherwise move with respect to a longitudinal axis of the traction band 110. In addition, or alternatively, the first and second attachment members 112, 114 may swivel or pivot about an axis perpendicular to the traction band 110, an axis parallel to the traction band 110 and/or any plane or angle of orientation between a perpendicular axis and a longitudinal axis to the traction band 110. As discussed below, the first and second swivels 116, 118 may be configured to alleviate and/or prevent torsional strain exerted on a target tissue or opposing wall of a body lumen as the margins of the target tissue are dissected. In various embodiments, an end of the first and second swivels may be attached to the respective ends of the traction band using a suitable glue, adhesive or resin, as are commonly known in the art. In some embodiments, the first and second swivels 116, 118 may be fixedly attached to opposite ends of the traction band 110 by an interference fit. For example, a portion of the respective first and second swivels 116, 118 may be disposed in a hollow end portion of the traction band 110. In some embodiments, the first and second swivels 116, 118 may be integrally formed with the traction band 110. In other embodiments, the first and second swivels 116, 118 may be fixedly attached to opposite ends of the traction band 110 by an internal coupling component, disposed within and extending along the traction band 110.

In one embodiment, the traction band 110 may be configured to move (e.g., stretch) from a first position (e.g., relaxed or non-tensioned) to a second position (e.g., extended, tensioned). By way of non-limiting example, the traction band 110 may have a length of approximately 2.5 to 4.5 cm when in the first position and may move a second position with maximum length of approximately 15.00 cm.

Figure 2A:
FIGS. 2A-2B provide perspective views of a tissue traction device, according to one embodiment of the present disclosure.
Figure 2B:

Referring to FIGS. 2A-2B, in one embodiment, a filament 120 (e.g., wire, connector, band, etc.) may be disposed along all or a portion of a length of the traction band 110 (e.g., along a longitudinal axis of the traction band between the first and second swivels 116, 118). In various embodiments, the filament 120 may be attached to an outer surface of the traction band 110 using a suitable glue, resin, or adhesive. In addition, or alternatively, the filament may be embedded within or integrally formed with the material(s) comprising the traction band 110. In some embodiments, the filament 120 may be fixedly coupled to the first and/or second swivels 116, 118.

In one embodiment, the filament 120 may comprise a substantially non-compliant (e.g., rigid or non-stretchable) material configured to limit the maximum length to which the traction band 110 may stretch. The filament 120 may prevent over-stretching of the traction band 110 beyond a predetermined breaking point. Non-limiting examples of such non-compliant materials may include hard plastics, non-compliant rubber or polymers, metals, and the like. In another embodiment, the filament 120 may comprise a substantially compliant or semi-compliant material configured to increase (e.g., supplement) the traction force exerted by the traction band 110 when stretched.

Although FIGS. 2A-2B depict a single filament 120 disposed in a linear configuration (e.g., when stretched) along the length of the traction band 110, in various embodiments, multiple filaments may be disposed along the traction band in a variety of patterns and/or configuration (e.g., zig-zag patterns, knitted patterns, wrapped helically around the traction band, etc.).

Figure 3A:
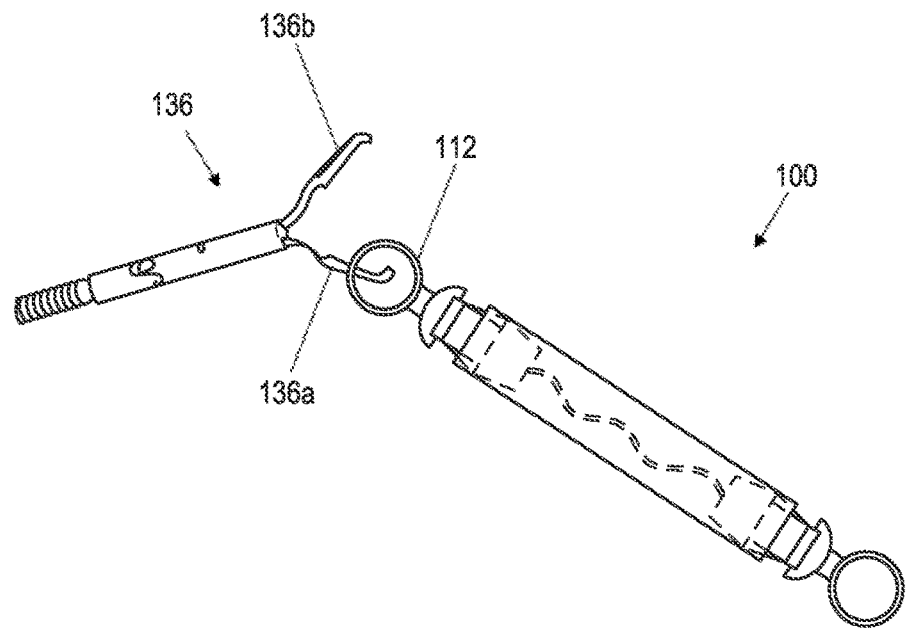
FIGS. 3A-3B provide perspective views of a tissue traction system, according to one embodiment of the present disclosure.
Figure 3B:
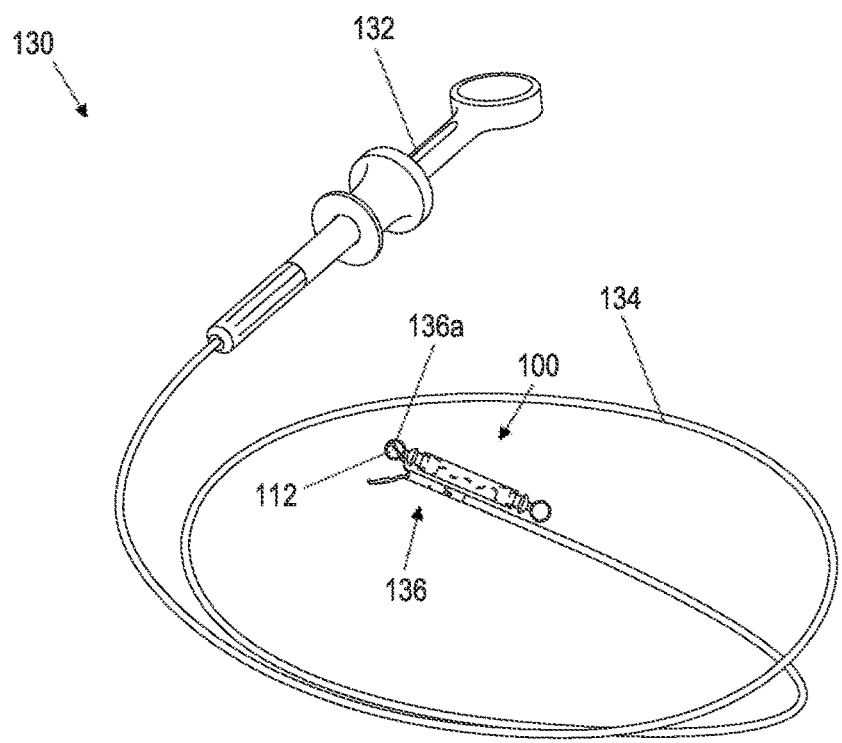

Referring to FIGS. 3A-3B, in one embodiment, a tissue traction device 100 of the present disclosure may be configured for use with a first endoscopic instrument 130. In various embodiments, the first endoscopic instrument 130 may include a handle 132 operatively attached to a proximal end of a flexible elongate sheath 134 (e.g., catheter, etc.) and a first tissue clip 136 releasably attached to a distal end of the flexible elongate sheath 134. The instrument 130 may be configured for use with an endoscope, bronchoscope, colonoscope, duodenoscope, ureteroscope, catheters, diagnostic or therapeutic tools or devices, or other types of medical devices. In one embodiment, the first tissue clip 136 may include first and second arms or jaws 136a, 136b configured to move upon actuation of the handle 132 between a first position (e.g., closed) and a second position (e.g., open). In various embodiments, in the closed position the arms or jaws 136a, 136b of the first tissue clip 136 may engage a target tissue 160 within a body lumen, e.g., a target tissue of the gastrointestinal (GI) tract. In various additional embodiments, the handle 132 may be further actuated to disengage (e.g., release) the first tissue clip 136 from the distal end of the sheath 134 such that the first tissue clip 136 remains engaged with the target tissue 160 after the first endoscopic instrument 130 has been removed from within the patient.

Figure 4A:
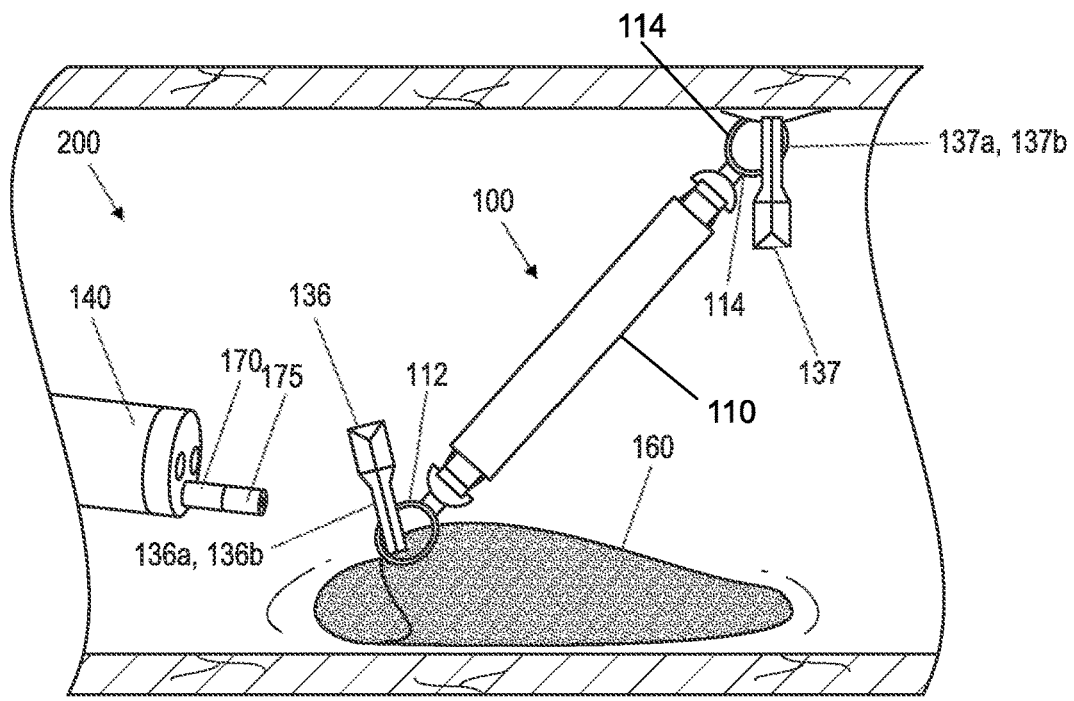
FIGS. 4A-4B provide a schematic illustration of a tissue resection procedure using a tissue traction device, according to one embodiment of the present disclosure.
Figure 4B:
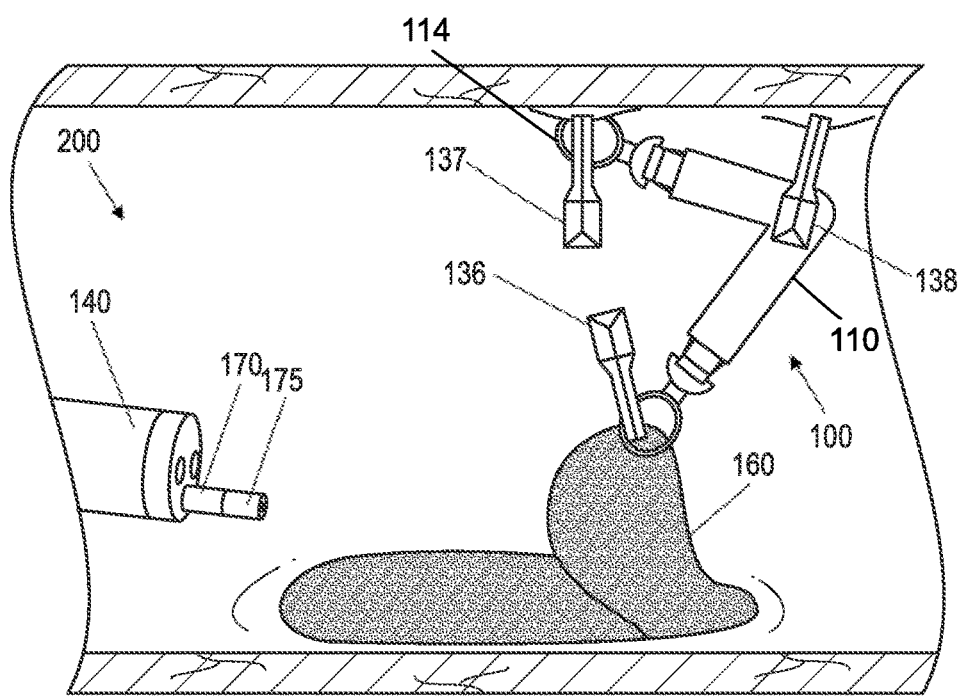

In one embodiment, a tissue traction system 200 of the present disclosure may include a first endoscopic instrument 130 slidably disposed within a working channel of a flexible elongate tubular member 140 (e.g., endoscope; FIG. 4A-4B). For example, the sheath 134 may extend through the working channel of an endoscope for deploying a clip 136 in a patient. As discussed above, the first endoscopic instrument 130 may include a first tissue clip 136 attached to a distal end of a flexible elongate sheath 134. In one embodiment, a tissue traction device 100 of the present disclosure may be attached to the first tissue clip 136 within the working channel of the flexible elongate member 140. For example, a tissue traction system 200 of the present disclosure may be assembled by advancing the first endoscopic instrument 130 through the working channel of the flexible elongate tubular member 140 such that the first tissue clip 136 attached to the distal end of the sheath 134 of the first endoscopic instrument 130 extends distally beyond a distal end of the flexible elongate tubular member 140. The handle 132 of the first endoscopic instrument 130 may be actuated to move the first tissue clip 136 from the first position to the second position, e.g., such that the first and second arms 136a, 136b are open/separated in a Y-shape. Either one of the first or second arms 136a or 136b may then be advanced through an opening of the first attachment member 112 of the tissue traction device 100. The handle 132 may then be actuated to move the first tissue clip 136 from the second position to the first position and the first endoscopic instrument 130 may be proximally retracted to load the tissue clip and tissue traction device within the working channel of the elongate tubular member, e.g., such that the first tissue clip 136 and tissue traction device 100 are disposed (e.g., protected, shielded, hidden, etc.) within the working channel of the elongate tubular member 140.

Referring to FIG. 4A, the tissue traction system 200 may then be advanced through a body lumen of a patient and the distal end of the flexible elongate tubular member 140 positioned adjacent to a target tissue 160. The first endoscopic instrument 130 may then be distally advanced through the working channel to position the tissue retraction device 100 and first tissue clip 136 attached thereto beyond the distal end of the elongate tubular member 140. The handle 132 may then be actuated to move the first tissue clip 136 from the first position to the second position and the open arms 136a, 136b placed in contact with a surface of the target tissue 160 (e.g., with either one of the first or second arms 136a or 136b extending through an opening of the first attachment member 112 of the tissue traction device 100, as discussed above). The handle 132 may then be actuated to move the first tissue clip 136 from the second position to the first position to engage (e.g., clamp) the first tissue clip 136, and the first attachment member 112 of the tissue traction device 100 attached thereto, with the target tissue 160. In one embodiment, the first tissue clip 136 may be directly engaged with the portion of the target tissue 160 on which a procedure is to be performed (e.g., tissue to be dissected). Alternatively, the first tissue clip 136 may be engaged with the target tissue 160 adjacent to the portion on which a procedure is to be performed (e.g., the portion being dissected). The handle 132 may then be actuated to disengage the first tissue clip from the sheath 134 of the first endoscopic instrument 130.

In one embodiment, the first endoscopic instrument 130 may then be withdrawn from within the working channel of the flexible elongate tubular member 140 and a second tissue clip 137 attached to the distal end of the sheath 134. The first endoscopic instrument 130 may then be advanced back through the working channel to position the second tissue clip 137 beyond the distal end of the flexible elongate tubular member 140. The handle 132 of the first endoscopic instrument 130 may then be actuated to move the second tissue clip 137 from the first position to the second position, e.g., such that the first and second arms 137a, 137b are open/separated in a Y-shape. Either one of the first or second arms 137a or 137b may then be advanced through an opening of the second attachment member 114 of the tissue traction device 100 within the body lumen. The first endoscopic instrument 130 may then be distally advanced through the working channel such that the traction band 110 of the tissue traction device 100 engaged with the first or second arms 137a, 137b of the second tissue clip 137 moves (e.g., stretches) from the first position to an extended/stretched second position. The arms 137a, 137b of the second tissue clip 137 may then be placed in contact with a wall of the body lumen opposite the target tissue 160. The handle 132 may then be actuated to move the second tissue clip 137 from the second position to the first position to engage (e.g., clamp) the second tissue clip 137, and the second attachment member 114 of the tissue traction device 100 attached thereto, with the wall of the body lumen opposite the target tissue 160. The handle 132 may then be actuated to disengage the second tissue clip 137 from the sheath 134 of the first endoscopic instrument 130, thereby placing the target tissue 160 under tension/traction by the stretched traction band 110 of the tissue traction device 100. Although the traction band 110 may have a maximum second (e.g., stretched) length of approximately 15.00 cm, in various embodiments sufficient traction force may be provided by a traction band having a second length of approximately 8.0 to 9.0 cm.

In various embodiments, the first endoscopic instrument 130 may then be removed (e.g., withdrawn) from the working channel of the elongate tubular member 140 and a second endoscopic instrument 170 advanced through the working channel to position a second medical device 175 (e.g., an electrocautery knife, resection tool, etc.) attached to a distal end of the second endoscopic instrument adjacent to the target tissue 160. A procedure may then be performed on the target tissue 160 (e.g., the target tissue may then be dissected) using the second medical device 175 while the tissue traction device 100 provides tension/traction on the target tissue 160. For instance, the tissue traction device 100 may provide tension/traction away from the cutting plane and without impeding/blocking visualization from the distal end of the flexible elongate tubular member 140.

Referring to FIG. 4B, in one embodiment, the direction or angle or amount of traction may be adjusted during the procedure using a third tissue clip 138. For example, a third tissue clip 138 may be attached to the distal end of the sheath 134 of the first endoscopic instrument 130 and the first endoscopic instrument advanced through a second working channel of the elongate tubular member 140 to position the third tissue clip 138 beyond the distal end of the elongate tubular member 140. The handle 132 of the first endoscopic instrument 130 may then be actuated to move the third tissue clip 138 from the first position to the second position, e.g., such that the first and second arms 138a, 138b are open/separated in a Y-shape. The first endoscopic instrument 130 may then be maneuvered to position the stretched traction band (e.g., engaged with the wall of the body lumen by the first and second tissue clips 136, 137) between the first and second arms 138a, 138b of the third tissue clip 138. The arms 138a, 138b of the third tissue clip 138 may then be placed in contact with another/second portion of the wall of the body lumen opposite the target tissue 160, drawing a portion of the traction band 110 towards the other/second portion of the wall of the body lumen to apply traction to the target tissue 160. The handle 132 may then be actuated to move the third tissue clip 138 from the second position to the first position to engage (e.g., clamp) the third tissue clip 138 (along with the traction band 110) with the other/second portion of the wall of the body lumen opposite the target tissue 160. The handle 132 may then be actuated to disengage the third tissue clip 138 from the sheath 134 of the first endoscopic instrument 130, thereby providing traction to the target tissue in a different direction or plane.

Figure 5A:
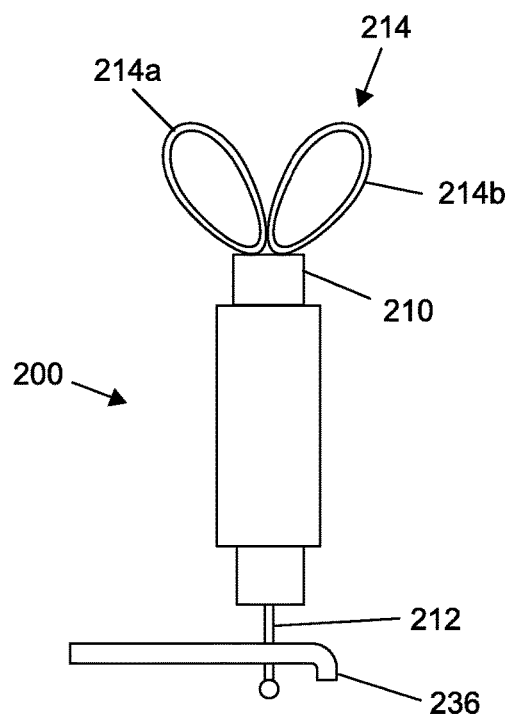
FIGS. 5A and 5B provide a perspective view of a tissue traction device according to another embodiment of the present disclosure.
Figure 5B:
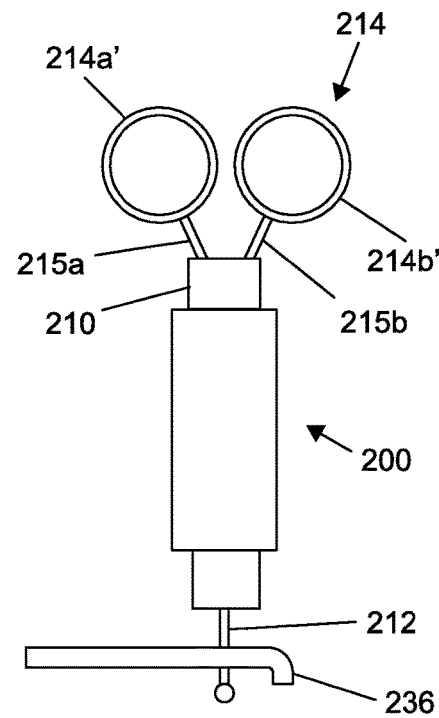

Referring to FIGS. 5A and 5B, in another embodiment, the direction or angle or amount of traction may be adjusted during the procedure using a third tissue clip and moving the position of the second end of the traction band (opposite the first end which is coupled to the target tissue). In various embodiments, once a first attachment member 212 (shown in cross-section with a jaw of a first tissue clip 236 extending therethrough) is coupled to target tissue 160, such as via a first tissue clip 236, the second end of the traction band 210 is extended to couple a second attachment member 214 at the second end of the traction band 210 to another/second portion of the wall of the body lumen opposite the target tissue 160 to apply traction to the target tissue 160. As illustrated in FIGS. 5A and 5B, more than one second attachment members 214 may be coupled directly or indirectly to the second end of the traction band. Referring to FIG. 5A, a traction device 200 is shown with at least two attachment members 214a, 214b, such as in the form of hoops or loops, may be coupled to the second end of the traction band 210. Referring to FIG. 5B, each attachment member 214a', 214b' may be coupled to the traction band 210 via a respective stem 215a, 215b. Additional attachment members with or without stems may be provided, and are not shown only for the sake of simplifying the illustrations of the embodiments and not with intent to limit the disclosure. A first attachment member 214a, 214a' may be initially coupled to a first anchoring tissue position (similar to as shown in FIG. 4A). If and when it is desired to modify traction, a third clip is used (such as the third clip 138 described with reference to FIG. 4B) to engage a different attachment member (such as attachment member 214b, 214b') at the second end of the traction band, such as attachment member 215b, 215b'. The first attachment member at the second end of the traction band may then be cut, either through the loop of the attachment member 214a (such as in the embodiment illustrated in FIG. 5A) or through the stem element 215a coupling the attachment member 214a' to the traction band 210 (such as in the embodiment illustrated in FIG. 5B). The third clip and next attachment member may then be engaged with another/second portion of the wall of the body lumen to apply traction to the target tissue 160 from a different direction/angle or with increased tension or otherwise.

In various embodiments, the multiple-attachment members coupled to the second end of the traction device are coupled independent of each other, and/or separately coupled to the traction device. As such, each attachment member may function independently of the others. In some embodiments, one or more of the multiple attachment members may be coupled to the traction device via a swivel connection allowing the attachment member to pivot or rotate about or otherwise move with respect to the longitudinal of the traction device.

Figure 6:
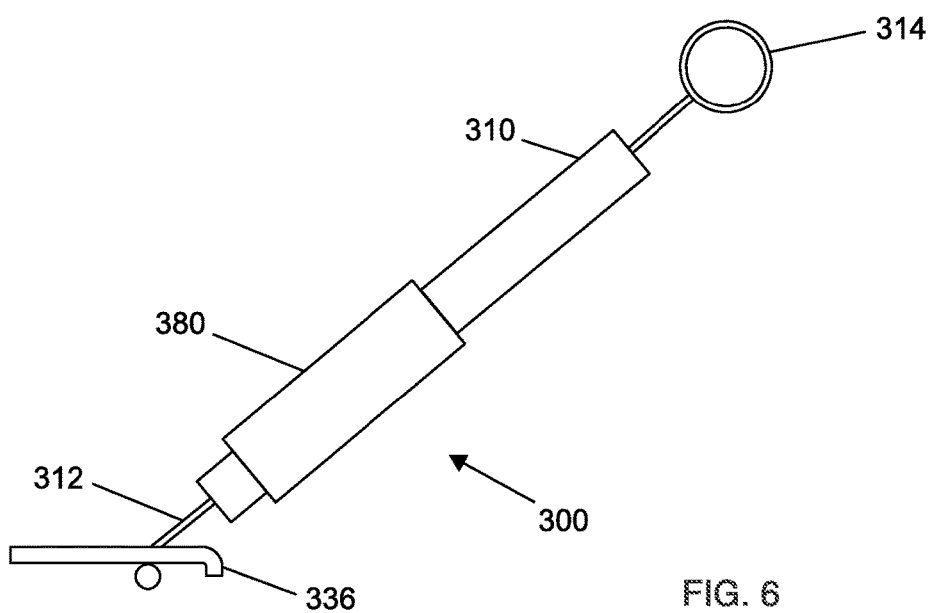
FIG. 6 provides a perspective view of an embodiment of a tissue traction device illustrating an aspect of the present disclosure.

In various embodiments, an overtube, such as, for example, the alignment member described in United States Patent Application Publication US2018/0263614, filed Mar. 19, 2018, and titled "Tissue Retraction Device and Delivery System", which application is hereby incorporated in its entirety herein for all purposes, may be provided over at least a portion of the traction band of a traction device formed in accordance with the present disclosure. Referring to FIG. 6, an overtube 380 is provided over the traction band 310 (shown in an extended configuration to apply traction) of a traction device 300. The overtube 380 may be provided to facilitate delivery of the traction device 300 through the working channel of the flexible elongate member 140, such as by inhibiting or preventing folding or wrapping of the traction band 310 upon itself (e.g., folding back on itself) while the traction device 300 is advanced and/or manipulated through the working channel. The overtube 380 may cover the majority or all of the traction band 310 during advancement of the traction device 310. However, once the first attachment member 312 (shown in cross-section with a jaw of a first tissue clip 336 extending therethrough) is coupled to target tissue 160, such as via a first tissue clip 336, and the second end of the traction band 310 is extended to couple the second attachment member 314 to another/second portion of the wall of the body lumen opposite the target tissue 160 to apply traction to the target tissue 160, the traction band 310 may extend beyond the end of the overtube 380, as illustrated in FIG. 6. In various embodiments, the overtube may be fixed adjacent to the first end of the traction device 300 (e.g., adjacent to the first attachment member 312, to which a first clip 336 may be pre-loaded, or later coupled, to attach the first attachment member to target tissue), such as by crimping (to the traction band or a swivel coupling the attachment member to the traction band or to another end element of the traction device), adhesive, or other connection known to those of ordinary skill in the art. Such fixing may be helpful in reliably positioning the overtube, such as if the target tissue is positioned above the endoscope.

In various embodiments, with the first tissue clip 136, 336 directly engaged with the portion of the target tissue 160 on which a procedure is to be performed (e.g., tissue being dissected), after the procedure has been completed (e.g., the target tissue has been fully dissected), the second tissue clip 137 (or second and third tissue clips 137, 138) may be detached from the opposing wall of the body lumen. In some embodiments, the clips arms may be separated by applying a sufficient amount of force (e.g., using forceps, etc.) to either the jaws and/or a proximal end to disengage the arms of the tissue clip. Excised target tissue 160 and attached tissue clips may then be removed from the patient through a working channel of the elongate tubular member 140. Alternatively, the traction band 110, 210, 310 or swivels 116, 118 may be cut (e.g., using the second medical device 175) and the second tissue clip (or second and third tissue clips 137, 138) left behind in the body lumen and expelled from the patient by the body's natural course. Or, the second attachment member 114, 214a, 214b, 214a', 214b', 314, or a stem 215a, 215b thereof, can be cut, releasing the traction device 200, 300 therefrom.

The present disclosure is not limited to a tissue traction device 100, 200, 300 attached to a first tissue clip 136, 236, 336 of a first endoscopic instrument 130 and loaded/pre-loaded within a working channel of an elongate tubular member 140. In various embodiments, some of steps involved in assembling the tissue retraction device and tissue clip(s) may occur outside of the patient's body, while some other steps involved in assembling the tissue retraction device and tissue clips(s) may occur inside the patient. The specific order and/or timing of any or all of these steps is not limited to the description of the present disclosure, but may be performed in a variety of different steps before, during or after a medical procedure. For example, in one embodiment, a tissue traction device 100, 200, 300 of the present disclosure may be loaded within the flexible elongate sheath 134 of the first endoscopic instrument 130, advanced through the working channel of an elongate tubular member 140 and ejected into the body lumen by distally advancing the first tissue clip 136, 236, 336 within the sheath 134. The first and second attachment members 112, 114, 214a, 214a,b, 214a', 214b', 314 of the tissue traction device 100, 200, 300 may then be engaged by respective first and second tissue clips 136, 137, 236, 336 within the body lumen and engaged (e.g., clamped) to the target tissue and opposing wall of the body lumen as discussed above. Alternatively, a tissue traction device 100, 200, 300 of the present disclosure may be pre-loaded within a biopsy cap. The pre-loaded biopsy cap may be secured to a proximal end of the elongate tubular member 140 and then distally advanced over/along an outer surface of the elongate tubular member to seal a working channel at a distal end of the elongate tubular member 140. The biopsy port and the tissue traction device 100, 200, 300 may then be removed from the biopsy cap within the body lumen using the first tissue clip 136, 236, 336.

In various embodiments, the second medical instrument of the present disclosure is not limited to a tissue resection element (e.g., electrocautery knife, etc.), but may include a variety of medical instruments configured to manipulate a target tissue under traction (e.g., ablative elements, biopsy needles, injection needles, scissors, graspers, etc.

In various additional embodiments, a traction band of the present disclosure is not limited to an elongate (e.g., rectangular) and/or planar (e.g., flat) configuration, but may include a variety of different shapes and/or configurations. For example, a traction band of the present disclosure may include a coiled or helical shape; a round, oblong or spherical shape; a square shape; a triangular shape, etc.

In various additional embodiments, the first and second attachment members 112, 114, 212, 214, 312, 314 may be engaged with a variety of different hemostasis (e.g., Resolution™ Clip, Boston Scientific Corp., Marlborough Mass.) and non-hemostasis tissue clips configured to secure/engage the disclosed tissue traction device to the wall of a body lumen. For example, a tissue clip contemplated for use with the disclosed tissue traction device may include a naturally open/biased configuration configured to move to a closed/clamped configuration upon actuation by a handle assembly. In addition, or alternatively, a tissue clip contemplated for use with the disclosed tissue traction device may include a naturally closed/biased configuration configured to move an open configuration upon actuation by a handle assembly. In addition, or alternatively, fasteners other than the described tissue clips may be used to secure/engage the first and second attachment members of the disclosed tissue traction device to the wall of a body lumen. Examples of fasteners may include, but are not limited to, those described in U.S. patent application Ser. No. 15/930,604 filed May 13, 2020, and titled "Tissue Clip Devices, Systems, and Traction Methods", along with its priority application Provisional Patent Application No. 62/847,599, filed May 14, 2019, and titled "Tissue Clip Devices, Systems, and Retraction Methods"; U.S. Patent Application Publication No. US2018/0263614, filed Mar. 19, 2018, and titled "Tissue Retraction Device and Delivery System", along with its priority applications U.S. Provisional Patent Application No. 62/506,780 filed May 16, 2017, and titled "Tissue Retraction Device and Delivery System," U.S. Provisional Application No. 62/473,957, filed Mar. 20, 2017, and titled "Tissue Retraction Device," and U.S. patent application Ser. No. 15/925,110, filed Mar. 19, 2018, and titled "Tissue Retraction Device and Delivery System"; U.S. Patent Application Publication No. 2020/0129181, filed Oct. 30, 2019, and titled "Clip Devices, Systems, and Methods for Engaging Tissue"; and U.S. Pat. No. 8,062,311, issued Nov. 22, 2011, and titled "Endoscopic Hemostatic Clipping Apparatus", all of which are herein incorporated by reference in their entireties and for all purposes. Other features and aspects of these patents and patent applications, as well as U.S. patent application Ser. No. 15/930,620, filed May 13, 2020, and titled "Tissue Traction Bands And Methods For Tissue Traction"; and U.S. patent application Ser. No. 15/930,607, filed May 13, 2020, and titled "Tether Traction Systems And Methods Of Use Thereof", which applications are herein incorporated by reference in their entireties for all purposes, may complement devices and methods of the present disclosure and may be used therewith.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope, and concept of the disclosure as defined by the appended claims.

What is claimed is:

1. A tissue traction device, comprising:
   a traction band comprising a compliant or semi-compliant material;
   a first attachment member pivotably attached to a first end of the traction band by a first swivel;
   a second attachment member pivotably attached to a second end of the traction band by a second swivel; and
   a filament having different stretching characteristics than the traction band disposed along a length of the traction band.

2. The tissue traction device of claim 1, wherein the compliant or semi-compliant material is selected from the group consisting of rubbers, latex, elastics and TPE, or combinations thereof.

3. The tissue traction device of claim 1, wherein the first and second attachment members comprise a compressible material selected from the group consisting of polymers, plastics, shape memory metals, shape memory alloys, or combinations thereof.

4. The tissue traction device of claim 1, wherein the first and second attachment members pivot around a longitudinal axis of the traction band via the first and second swivels, respectively.

5. The tissue traction device of claim 1, wherein the traction band is configured to move from between a configuration having a length of approximately 2.5 to 4.5 cm and a second configuration having a maximum length of approximately 15.00 cm.

6. The tissue traction device of claim 1, wherein the filament comprises a substantially non-compliant material configured to limit a maximum extended length of the traction band.

7. The tissue traction device of claim 1, wherein the filament comprises a substantially compliant or semi-compliant material configured to increase a traction force of the traction band.

8. A tissue traction system, comprising:
   a flexible elongate tubular member defining a working channel therethrough;
   a first instrument disposed within the working channel, wherein the first instrument includes a first tissue clip configured to engage tissue and releasably attached to a distal end of the first instrument;
   a tissue traction device disposed within the working channel;
   a first attachment member configured to be engaged by a tissue clip and pivotably attached to a first end of the tissue traction device by a first swivel; and
   a second attachment member configured to be engaged by a tissue clip and pivotably attached to a second end of the tissue traction device by a second swivel.

9. The tissue traction system of claim 8, wherein the first tissue clip is releasably attachable to the first attachment member of the tissue traction device.

10. The tissue traction system of claim 8, wherein the first tissue clip at a first end of the tissue traction device is positionable in a body lumen, and wherein a second tissue clip is positionable in the body lumen and attachable to a second end opposite of the first end of the tissue traction device.

11. The tissue traction system of claim 10, wherein a third tissue clip is positionable in the body lumen and attachable to a portion of the tissue traction device.

12. The tissue traction system of claim 8, wherein the tissue traction device includes a traction band comprising a compliant or semi-compliant material.

13. A method, comprising:
   inserting into a body lumen, a tissue traction device loaded onto a first tissue clip of a first instrument with the first tissue clip engaged with an attachment member pivotably attached to a first end of the tissue traction device by a first swivel;
   advancing the first instrument through a working channel of an elongate tubular member and beyond a distal end of the elongate tubular member;
   engaging a target tissue of the body lumen with the first tissue clip to secure a first end of the tissue traction device to a wall of the body lumen; and
   releasing the first tissue clip from the first instrument.

14. The method of claim 13, wherein the tissue traction device comprises a compliant or semi-compliant traction band with a filament having different stretching characteristics than the traction band disposed along the length of the traction band.

15. The method of claim 13, further comprising withdrawing the first instrument from within the working channel of the elongate tubular member and attaching a second tissue clip to the distal end of the first instrument.

16. The method of claim 15, further comprising:
   advancing the first instrument through the working channel of the elongate tubular member and beyond a distal end of the elongate tubular member; and
   engaging the wall of the body lumen with the second tissue clip to secure a second end of the tissue traction device to the wall of the body lumen, wherein the first and second tissue clips are engaged with opposite sides of the body lumen.

17. The method of claim 16, further comprising releasing the second tissue clip from the first instrument.

18. The method of claim 17, further comprising manipulating the target tissue with a medical device attached to a distal end of a second instrument.

19. The tissue traction system of claim 12, further comprising a filament comprised of a substantially non-compliant material configured to limit a maximum extended length of the traction band.

20. The tissue traction device of claim 12, further comprising a filament comprised of a substantially compliant or semi-compliant material configured to increase a traction force of the traction band.

* * * * *